United States Patent

Clark et al.

[11] Patent Number: 5,837,256
[45] Date of Patent: Nov. 17, 1998

[54] METHOD FOR TREATMENT OF LUPUS NEPHRITIS

[76] Inventors: William F. Clark, 1132 Richmond Street, London, Ontario, Canada, N6A 3K8; Anwar Parbtani, 418 Rippleton Rd., London, Ontario, Canada, N6G 1L3

[21] Appl. No.: 770,147

[22] Filed: Dec. 19, 1996

Related U.S. Application Data

[60] Provisional application No. 60/009,031 Dec. 21, 1995.

[51] Int. Cl.[6] .................................................. A61K 31/045
[52] U.S. Cl. ........................................ 424/195.1; 514/885
[58] Field of Search ............................. 424/78.08, 195.1; 514/885

[56] References Cited

PUBLICATIONS

Bakke, JE and Klosterman, HJ: "A New Diglucoside From Flaxseed" *Proc. North Dakota Acad. Sci. 10*, 18–22, 1956.
Klosterman, HJ and Smith, F: "The Isolation of β–Hydroxy–β–Methylglutaric Acid From the Seed of Flax", *J. Am. Chem. Soc. 76*, 1229–1230, 1954.
MacRae, WD and Towers, GHN: "Biological Activites of Lignans", *Phytochemistry*, vol. 23, No. 6, pp. 1207–1220, 1984.
Harris, RK and Haggerty, WJ: "Assays for Potentially Anticarcinogenic Phytochemicals in Flaxseed", *Cereal Foods World*, vol. 38, No. 3, pp. 147–151, 1993.
Bambagiotti–Alberti, M et al.,: "Revealing the Mammalian Lignan Precursor Secoisolariciresinol Diguclosiside in Flax Seed by Ionspray Mass Spectrometry", *Rapid Communications in Mass Spectrometry*, vol. 8, pp. 595–598, 1994.
Obermeyer, WR et al.,: "Chemical Studies of Phytoestrogens in Flas and Chaparral", *Society for Experimental Biology and Medicine*, pp. 6–12, 1995.

*Primary Examiner*—Peter F. Kulkosky
*Attorney, Agent, or Firm*—Rosenthal & Osha L.L.P.

[57] ABSTRACT

It has been found that by administering secoisolariciresinol [2,3-bis(3-methyl-4-hydroxybenzyl)butane-1,4-diol] from flaxseed in substantially pure form to a human or non-human animal, lupus nephritis can be controlled. The secoisolariciresinol (Seco) may be used per se or in the form of secoisolariciresinol diglucoside (SDG). Both compounds may be extracted from flaxseed and the SDG converts to Seco in the gut of a human or animal.

9 Claims, 1 Drawing Sheet

METHOD FOR TREATMENT OF LUPUS NEPHRITIS

BACKGROUND OF THE INVENTION

This invention relates to a method for the treatment of lupus nephritis.

Lupus nephritis is considered in medical circles to be the "classical" auto-immune disease in which the patient's immune system attacks his/her own organs. It has been estimated that 45–75% of lupus patient's eventually suffer from some form or other of kidney damage. Lupus varies greatly in severity from mild cases requiring minimal intervention to those in which significant damage occurs to vital organs such as lungs, kidneys, heart and brain, and which ultimately can be fatal. Lupus is predominantly a female disease, an approximate female to male ratio being 9:1. In North America, it is estimated to affect 1 in 500 female mainly between the age of 20 to 40 years. Treatment is directed at controlling the symptoms with the hope of putting the disease into remission. There are several chemotherapeutic agents in commercial use and available for remedial purposes. Most of these agents are not without side effects, some of which are severe and debilitating to the patient. Some non-steroidal anti-inflammatory agents may cause stomach upsets and changes in kidney function which can mimic some lupus symptoms themselves. Some antimalarial drugs, when required at high dosage levels over prolonged time frame, may accumulate in the retina and cause loss of vision. Certain steroidal preparations are used for their anti-inflammatory activity. These can exhibit side effects such as pronounced swelling of the face and abdomen, weight gain, excessive growth of body hair, cataracts, osteoporosis and heart attacks. Use of immunosuppressants can have serious side effects such as changes in bone marrow, increased risk of infection to which the body normally shows resistance and a slight increase in the risk of developing certain types of cancer. There is no known cure for lupus.

Several reports have appeared in the scientific and medical literature concerning the ability of ground flaxseed to act as a mediator in the partial control of Lupus nephritis. At a level of intake of up to 30 grams per day, ground flaxseed has been shown to reduce the total cholesterol and LDL cholesterol levels by 12% and improve renal function in patients with lupus nephritis [(Clark, Parbtani et al., (1995) Flaxseed: A potential treatment for lupus nephritis, *Kidney International* 48: 475–480]. Beyond this intake level, side effects are evident such as Taxation probably due to increased fibre/mucilage intake.

Flaxseed is known to contain certain chemical entities such as alpha-linolenic acid which has been shown to lower LDL cholesterol, cell mediated immunity, PAF production by PMN leucocytes and platelet aggregation. Further studies have revealed that in a survey of foodstuffs for their ability to produce enterodiol and enterolactone (both mediators of cancer control mechanisms), flax was 60 times greater than the next ranking entry in its ability to produce these mediators. Enterodiol and enterolactone are trivially referred to as lignans and contain a structural backbone of dibenzylbutane. The most abundant lignan detected in flax is secoisolariciresinol diglucoside (SDG). It is known that when SDG is ingested, it is enzymatically hydrolyzed to the aglycone and transformed by intestinal microflora into enterodiol and enterolactone.

The existence of SDG has been known for 40 years and its extraction and purification were described at the laboratory level by Bakke and Klosterman (1956), A new diglucoside from flaxseed, *Proceedings of the North Dakota Academy of Science* 10: 18–22. However, most studies with SDG, and with other lignan types from other plant sources, have remained in the realm of scientific curiosity, since there has never been a demonstrated approach to the economical extraction and purification of this component.

Although the consumption of whole ground flaxmeal may offer some potential for the control or alleviation of certain medical disorders, a major drawback lies in the fact that only up to 30–45 g of this product can be consumed on a daily basis. The limitation is due to some readily apparent side effects such as increased Taxation, believed due to the presence of a mucilaginous substance, and also to progressive weight gain resulting from the rather high caloric value of the oil component. Flax contains upwards of 40% oil. The use of whole ground flaxseed or meal is also restricted in part because of the presence of cyanogenic glycosides present in the seed.

In Westcott and Muir, U.S. patent application Ser. No. 08/415,050, filed Mar. 31, 1995, there is described a practical method of extracting and purifying SDG, the principal lignan from flax.

The purpose of the present invention is to provide a method of using flaxseed for treatment of lupus nephritis without the aforementioned drawbacks of Taxation, cyanogenic glycosides, and caloric loads.

SUMMARY OF THE INVENTION

In accordance with this invention, it has been found that by administering secoisolariciresinol [2,3-bis(3-methyl-4-hydroxybenzyl)butane-1,4-diol] from flaxseed in substantially pure form to a human or non-human animal, lupus nephritis can be controlled. This is achieved without the undesirable side effects of Taxation, cyanogenic glycosides and caloric loads.

The secoisolariciresinol (Seco) may be used per se or in the form of secoisolariciresinol diglucoside (SDG). It is known that SDG is a precursor for Seco, as well as for the mammalian lignans, enterodiol and enterolactone, and it has been found that when SDG is orally administered to a human or animal, it is converted to secoisolariciresinol in the gut of the human or animal. The SDG has the advantage over Seco for oral administration that SDG has greater water solubility.

The SDG is typically used at a high degree of purity of over 90%, with a purity of over 95% being the preferred. It can be administered orally or intravenously, and has been found to be highly effective when administered in a daily oral dosage of about 20 to 100 mg/kg of body weight. The oral doses may conveniently be in the form of tablets or capsules and the SDG may be used together with a variety of pharmaceutically acceptable diluents or carriers.

SDG may be obtained from flaxseed by an extraction technique, such as that described in Westcott and Muir, U.S. patent application Ser. No. 08/415,050, filed Mar. 31, 1995 (incorporated therein by reference). The SDG may be converted to secoisolariciresinol by incubation with β-glucuronidase. It is also possible to obtain secoisolariciresinol directly from flaxseed using β-glucuronidase as described by obermeyer et al., Chemical studies of phytoestrogens and related compounds in dietary supplements: flax and chaparral, *Society for Experimental Biology and Medicine*, Vol. 208, 1995 (incorporated herein by reference).

DESCRIPTION OF THE PREFERRED EMBODIMENTS

Figure 1:
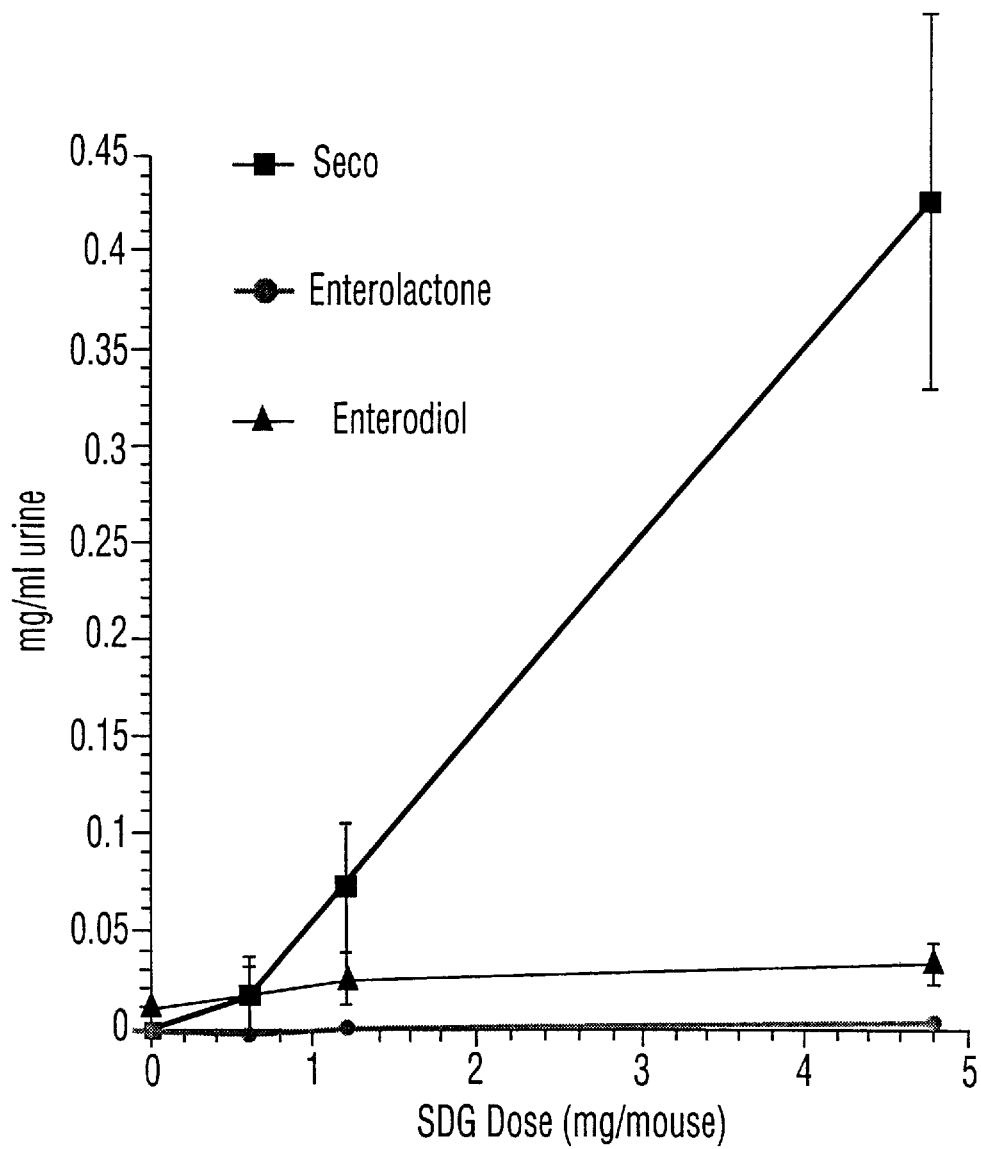
FIG. 1 is a graph of lignin content in urine samples according to Example 7.

The invention is further illustrated by the following non-limiting Examples. These Examples also serve to differentiate the specificity of action of SDG from the more general action of either whole ground flaxseed, defatted flax meal and flax oil, rich in alpha-linolenic acid as well as mucilage and fibre.

EXAMPLE 1

The MRL/lpr mouse model of lupus was chosen to study the effects of SDG on experimental nephritis since it represents the human disease in terms of immune and inflammatory reactions, and age-related renal function deterioration leading to progressive glomerular scarring. The experimental design for all evaluations of the effects of SDG on physiological function is given in Table 1.

TABLE 1

Experimental design for the evaluation of the effect of SDG on the physiological functions and mortality in the MRL/lpr mouse: Number of mice used and assigned for each age interval of the study.

| Age | 6 weeks | 14 weeks | 22 weeks | NUMBER OF MICE ASSIGNED |
|---|---|---|---|---|
| Baseline Study Group | 10 | | | 10 |
| Vehicle Control Group | | 10 | 10 | 25* |
| Low-Lignan Group (600 μg/day) | | 10 | 10 | 25* |
| High-Lignan Group (1200 μg/day) | | 10 | 10 | 25* |

*For a 3 group comparison by ANOVA, the appropriate sample size was calculated to be 10 mice per experimental group per age-interval. Extra 5 mice were set aside in anticipation of loss due to mortality/morbidity associated with the disease.

Mice were obtained at 5 weeks of age from Jackson Laboratories, Me., U.S.A., and acclimatized for one week. From 6 weeks of age onwards, all groups were gavaged with 200 μl/day of water. The appropriate amount of SDG was dissolved in the water to administer either the low-dose (600 μg/day) or the high-dose (1200 μg/day) of SDG.

All procedures relating to the care and welfare of test animals within this experimental protocol conformed to the following Standard Operating Procedures (SOP) approved by the Council of Animal Care, University of Western Ontario, London, Ontario, Canada:

SOP 301-10: Holding period post admission

SOP 340-01: Surgical Preparation, rodents

SOP 330-01: Post-operative care, rodents.

Mortality/morbidity was recorded weekly. For humane reasons, any animal which became morbid was sacrificed and was included in the mortality count. Morbidity was judged according to the SOP-321-01: Criteria for Early Termination of Experiment which included signs such as hunched posture, loss of appetite and/or severe weight loss, exudating skin lesions and immobility/severe state of lethargy.

EXAMPLE 2

This example illustrates the effect of SDG on the body weight of MRL/lpr lupus mice in compared to the control group. The daily dosage was administered over a 17-week period (6 to 22 weeks of age).

TABLE 2

Effect of SDG on Body Weight (g) (mean = SD)

| Age | wk5 | wk7 | wk9 | wk11 | wk13 | wk15 | wk17 | wk19 | wk21 | w22 |
|---|---|---|---|---|---|---|---|---|---|---|
| Control | 25 ± 2 | 26 ± 2 | 27 ± 2 | 30 ± 3 | 32 ± 3 | 35 ± 4 | 37 ± 3 | 37 ± 3 | 39 ± 3 | 37 ± 3 |
| Low-Lignan gp (600 μg/day) | 25 ± 2 | 26 ± 3 | 27 ± 3 | 29 ± 3 | 31 ± 3 | 33 ± 3 | 36 ± 3 | 37 ± 3 | 38 ± 4 | 38 ± 3 |
| High-Lignan gp (1200 μg/day) | 25 ± 2 | 26 ± 2 | 27 ± 2 | 29 ± 2 | 31 ± 3 | 34 ± 3 | 37 ± 3 | 38 ± 3 | 39 ± 3 | 38 ± 3 |

The data of Table 2 show that there was no significant difference in the body weight gain in the different treatment groups which was in keeping with our observation of no significant difference in either the food or water intake.

EXAMPLE 3

This example shows the effect of SDG on the time of onset and prevalence of proteinuria which is an early sign and a measure of severity of renal involvement in the lupus mouse.

TABLE 3

The effect of SDG on the onset and prevalcen of proteinuria (% of mice with ≧ 2 proteinuria on Albustix ® )

| Age | wks 6–8 | wk 9 | wk 10 | wk 11 | wk 12 | wk 13 | wk 14 | wk 15 | wk 16 | wk 17 | wk 18 | wk 19 | wk 20 | wk 21 |
|---|---|---|---|---|---|---|---|---|---|---|---|---|---|---|
| Control | 0 | 4 | 8 | 8 | 8 | 8 | 33 | 43 | 36 | 46 | 38 | 38 | 53 | 46 |
| Low-Lignan gp (600 μg/day) | 0 | 0 | 0 | 0 | 0 | 0 | 17 | 21 | 21 | 23 | 38 | 38 | 38 | 27 |
| High-Lignan gp (1200 μg/day) | 0 | 0 | 0 | 4 | 4 | 4 | 4 | 7 | 7 | 7 | 21 | 36 | 50 | 43 |

Gavaging was commenced at the age of 6 weeks in all groups.

The data support the view that both low and high dosages of SDG delay the onset of proteinuria and reduce the prevalence of proteinuria.

EXAMPLE 4

This example illustrates the effect of SDG on the glomerular filtration rate (GFR) assessed by $^{14}$C-inulin clearance. The data are given in Table 4.

TABLE 4

The effect of SDG on the GFR (ml/min/kg body weight) (mean = SD)

| BASELINE 6 wks of age | TREATMENT GROUPS | 14 wks of age | 22 wks of age |
|---|---|---|---|
| 7.66 ± 2.82 (n = 9) | Control | 6.10 ± 2.50 (n = 9) | 3.47 ± 1.31a (n = 9) |
| | Low-Lignan (600 μg/day) | 7.41 ± 3.88 (n = 10) | 4.81 ± 1.49 (n = 10) |
| | High-Lignan (1200 μg/day) | 8.09 ± 2.74 (n = 9) | 5.33 ± 3.16 (n = 10) | a:Significantly lower compared to the baseline value obtained at 6 weeks of age.

These data suggest that SDG attenuates the decline of renal function (GFR) which was observed in the vehicle treated control group. The data also indicate a dose-dependant benefit of SDG.

EXAMPLE 5

The MRL/lpr mice exhibit sever, age-related lymphadenopathy. We therefore examined the effects of low and high dosages of SDG on a deep cervical lymph node in these animals. The data are given in Table 5.

TABLE 5

The effects of SDG on cervical lymph node weights (mg) in MRL/lpr mice

| BASELINE 6 wks of age | TREATMENT GROUPS | 14 wks of age | 22 wks of age |
|---|---|---|---|
| 13 ± 5 (n = 10) | Control | 112 ± 75a (n = 10) | 190 ± 93a (n = 10) |
| | Low-Lignan 11 600 μg/day) | 97 ± 69a (n = 10) | 251 ± 91a (n = 10) |

TABLE 5-continued

The effects of SDG on cervical lymph node weights (mg) in MRL/lpr mice

| BASELINE 6 wks of age | TREATMENT GROUPS | 14 wks of age | 22 wks of age |
|---|---|---|---|
| | High-Lignan (1200 μg/day) | 71 ± 65 (n = 10) | 211 ± 58a,b (n = 10) | a:significantly greater than the baseline values
b:significantly greater than 14 week values for animals receiving same treatment.

The data was non-normally distributed therefore, a non parametric (Kruskal-Wallis) statistical test was used. The only beneficial difference observed was that the high dose of SDG attenuated the increase in lymph node weight at/up to 14 weeks of age.

EXAMPLE 6

The MRL/lpr mouse also exhibits a spontaneous age-related splenomegaly. We therefore examined the effects of low and high dosages of SDG on spleen weight. The spleen weight index was obtained as a ratio of spleen to body weight (×100). The data are given in Table 6.

TABLE 6

The effect of SDG on the Spleen Weight/Body Weight Ratio (×100)

| BASELINE 6 wks of age | TREATMENT GROUPS | 14 wks of age | 22 wks of age |
|---|---|---|---|
| 0.33 ± 0.07 (n = 10) | Control | 1.02 ± 0.33a (n = 10) | 1.72 ± 0.46a,b (n = 10) |
| | Low-Lignan (600 μg/day) | 0.93 ± 0.33a (n = 10) | 1.89 ± 0.39a,b (n = 10) |
| | High-Lignan (1200 μg/day) | 0.77 ± 0.26a (n = 10) | 1.74 ± 0.35a,b (n = 10) |

Data analyzed by ANOVA followed by Bonferroni t-tests

The data of Example 6 show that there was no significant difference in the spleen weight index in the different groups, however at 14 weeks age-interval, the high dose SDG group showed a moderately smaller spleen weight gain compared to other groups.

The results cited in Examples 5 and 6 taken together indicate moderate benefits of SDG in terms of reducing cell proliferation, a marker of immune and inflammatory activity of the auto-immune diseases.

EXAMPLE 7

Using the same preparations and procedures as described in Examples 1–6, mice were gavaged with water containing SDG. The mice were dosed with the SDG in amounts of 0.6, 1.2 and 4.8 mg/mouse.

Urine samples from the mice were then analysed for lignans. The results are shown in FIG. 1, which shows the contents of secoisolariciresinol, enterolactone and enterodiol in the urine. These results indicate that the secoisolariciresinol concentrations in the urine are SDG dose dependent, while only traces of the mammalian lignans are present. Since it is generally accepted that diglycosides, such as SDG, are not absorbed across the gut wall, the above results indicate that in oral administration of SDG, the active compound is secoisolariciresinol.

EXAMPLE 8

Secoisolariciresinol was also obtained by incubating purified SDG with β-glucuronidase from Heliz pornatia (Type H-1, Sigma Chemical). After the incubation, secoisolariciresinol was recovered from the incubation mixture by ethyl acetate extraction. The secoisolariciresinol thus obtained was then further purified by prep HPLC and freeze dried out of water.

What is claimed is:

1. A method for the treatment of lupus nephritis which comprises administering to a patient an effective amount of secoisolariciresinol or secoisolariciresinol diglucoside (SDG) in substantially pure form, wherein the secoisolariciresinol or secoisolariciresinol diglucoside in substantially pure form has been demonstrated to be effective in the MRL/lpr mouse model of lupus nephritis.

2. A method for the treatment of lupus nephritis which comprises administering to a patient an effective amount of secoisolariciresinol diglucoside in substantially pure form.

3. A method according to claim 2 wherein the SDG has a purity of at least 90%.

4. A method according to claim 2 wherein the SDG has a purity of at least 95%.

5. A method according to claim 4 wherein the SDG is obtained from flaxseed.

6. A method according to claim 4 wherein the SDG is administered orally.

7. A method according to claim 4 wherein the SDG is administered in a daily dosage of about 20 to 100 mg/kg of body weight.

8. A composition for treatment of lupus nephritis consisting essentially of substantially pure secoisolariciresinol or secoisolariciresinol diglucoside together with a pharmaceutically acceptable diluent or carrier.

9. A composition according to claim 8 in the form of a capsule or tablet.

* * * * *